US005837672A

United States Patent [19]
Schenk et al.

[11] Patent Number: 5,837,672
[45] Date of Patent: *Nov. 17, 1998

[54] METHODS AND COMPOSITIONS FOR THE DETECTION OF SOLUBLE β-AMYLOID PEPTIDE

[75] Inventors: Dale B. Schenk, Pacifica, Calif.; Michael G. Schlossmacher, Vienna, Austria; Dennis J. Selkoe, Jamaica Plain, Mass.; Peter A. Seubert, South San Francisco; Carmen Vigo-Pelfrey, Mountain View, both of Calif.

[73] Assignees: Athena Neurosciences, Inc., So. San Francisco, Calif.; Eli Lilly and Company, Indianapolis, Ind.; Brigham and Women's Hospital, Boston, Mass.

[*] Notice: The term of this patent shall not extend beyond the expiration date of Pat. No. 5,766,846.

[21] Appl. No.: 456,347

[22] Filed: Jun. 1, 1995

Related U.S. Application Data

[60] Division of Ser. No. 437,067, May 9, 1995, Pat. No. 5,593,846, and a continuation-in-part of Ser. No. 911,647, Jul. 10, 1992, abandoned.

[51] Int. Cl.[6] .......................... A61K 31/00; A61K 38/00
[52] U.S. Cl. .................................. 514/2; 514/2; 514/42; 514/76.9; 514/222.2; 424/520; 435/7.9; 435/7.2; 436/518; 436/811
[58] Field of Search .............................. 435/7.9, 4, 7.8, 435/6, 7.1, 7.2, 7.4; 436/518, 547, 548, 63, 811; 424/9.1, 184.1, 277.1, 520; 514/2, 42, 169, 222.2

[56] References Cited

U.S. PATENT DOCUMENTS

| | | | |
|---|---|---|---|
| 4,486,530 | 12/1984 | David et al. | 435/7.91 |
| 4,666,829 | 5/1987 | Glenner et al. | 435/6 |
| 5,221,607 | 6/1993 | Cordell et al. | 435/6 |
| 5,387,742 | 2/1995 | Cordell | 800/2 |
| 5,441,870 | 8/1995 | Seubert et al. | 435/7.1 |
| 5,538,845 | 7/1996 | Knops et al. | 435/6 |

FOREIGN PATENT DOCUMENTS

| | | |
|---|---|---|
| 444856 | 9/1991 | European Pat. Off. |
| WO 90/12870 | 11/1990 | WIPO |
| WO 90/12871 | 11/1990 | WIPO |
| WO 91/19810 | 12/1991 | WIPO |
| WO 93/08264 | 9/1993 | WIPO |
| WO 94/01772 | 1/1994 | WIPO |

OTHER PUBLICATIONS

Allsop, et al., "Immunohistochemical evidence for the derivative of a peptide ligand from the amyloid Beta protein precursor of Alzheimer disease", *Proc. Natl. Acad. Sci. USA*, 85:2790–2794, Apr. 1988.

Anderson, J.P., et al., "Exact cleavage site of Alzheimer amyloid presursor in neuronal PC–12 cells", *Neuroscience Letters*, 128:126–128, 1991.

Barrow and Zagorski, *Science*, 253:179, 1991.

Boller, et al., "Biological Markers of Alzheimer's Disease", *Springer–Verlag* (Berlin), pp. 24–29, 1989.

Bullock, et al., "Techniques in Diagnostic Pathology" vol. 2, *Academic Press* (London), pp. 100–112, 1991.

Burdick, et al., *J. Biol. Chem.*, 267:546, 1992.

Castano, et al., "In Vitro formation of amyloid fibrils from two synthetic peptides of different lengths homologous to Alzheimer's disease Beta protein", *Biochem. Biophys. Res. Comm.*, 141(2):782–789, Dec. 15, 1986.

Citron, M., et al., "Mutation of the Beta–amyloid precursor protein in familial Alzheimer's disease increases Beta–protein production", *nature*, 360:672–674.

Esch, et al., "Cleavage of amyloid Beta–peptide during constitutive processing of its precursor", *Science*, 248:1122–1124, Jun. 1, 1990.

Glenner and Wong, *Biochem. Biophys. Res. Comm.*, 120:885, 1984.

Glenner and Wong, *Biochem. Biophys. Res. Comm.*, 122:1131, 1984.

Haass, et al., "Amyloid Beta–peptide is produced by cultured cells during normal metabolism", *Nature*, vol. 359 pp. 322–325, Sep. 24, 1992.

Harlow and Lane, "*Antibodies A Laboratory Manual*", Cold Spring Harbor Laboratory, pp. 578–582, 1988.

Henriksson, et al., *J. Neurochem.*, 56:1037, 1991.

Hilbich, et al., *J. Mol. Biol.*, 218:149, 1991.

Joachim, et al., *Brain Res.*, 474:100, 1988.

Joachim, et al., *Nature*, 341:226, 1989.

Kim and Wisniewski, "*Techniques in diagnostic pathology*", ed. Bullock et al., Academic Press–Boston, p. 106.

Kirschner, et al., "Synthetic peptide homologous to Beta–p–rotein from Alzheimer disease forms amyloid–like fibrils in vito", *Proc. Natl. Acad. Sci. USA*, 84:6953–6957, Oct. 1987.

Ksiezak–Reder, et al.,*J. Biol. Chem.*, 263:7943–7947, 1988.

Lee, et al., *Science*, 251:675–678, 1991.

Masters, et al., *Proc. Natl. Acad. Sci. USA*, 82:4245, 1985.

McKhann, et al., "Clinical diagnosis of Alzheimer's disease", *Neurology*, 34:939–944, Jul. 1984.

Palmert, et al., *Proc. Natl. Acad. Sci. USA*, 86:6338, 1989.

Palmert, et al., *Neurology*, 40:1028, 1990.

(List continued on next page.)

*Primary Examiner*—Jasemine C. Chambers
*Assistant Examiner*—Karen M. Hauda
*Attorney, Agent, or Firm*—Townsend and Townsend and Crew LLP

[57] ABSTRACT

Soluble β-amyloid peptide (βAP) is measured in biological fluids at very low concentrations, typically in the range from 0.1 ng/ml to 10 ng/ml. The measurement of βAP concentrations in animals or conditioned medium from cultured cells can be used for drug screening, where test compounds are administered to the animals or exposed to the cultured cells and the accumulation of βAP in the animal or culture medium observed. It has been found that elevated levels of βAP in body fluids, such as blood and cerebrospinal fluid, is associated with the presence of a βAP-related condition in a patient, such as Alzheimer's Disease. Methods for diagnosing and monitoring βAP-related conditions comprise measuring the levels of βAP in such body fluids from a patient.

14 Claims, 8 Drawing Sheets

OTHER PUBLICATIONS

Pardridge, et al., *Biochem. Biophys. Res, Commun.*, 145:241, 1987.

Pennisi, et al., "A molecular whodunit", *Science News*, vol. 145 No. 1, pp. 8–11, Jan. 1, 1994.

Podlisny, et al., *Biochem. Biophys. Res. Comm.*, 167:1094, 1990.

Rumble, et al., *New Eng. J. of Med.*, 320:1446, 1989.

Schlossmacher, et al., *Neurobiol. Aging*, 13:421, 1992.

Selkoe, et al., *J. Neurochem.*, 46:1820, 1986.

Selkoe, et al., *Neurobiol. Aging*, 7:425, 1986.

Selkoe, et al., *Neurobiol. Aging*, 10:387, 1989.

Seubert, et al., "Isolation and quantification of soluble Alzheimer's Beta–peptide from biological fluids", *Nature*, vol. 359 pp. 325–327, Sep. 24, 1992.

Seubert, et al., "Secretion of Beta–amyloid precursor protein cleaved at the amino terminus of the Beta–amyloid peptide", *Nature*, 361:260–263, 1993.

Ueda, et al., *J. Neuroscience*, 10:3295–3304, 1990.

Weidemann, et al., *Cell*, 57:115, 1989.

Wisniewski, "*Alzheimer's disease*", ed. Becker et al., p. 206.

Wolozin, et al., *Science*, 232:648–650, 1986.

Wong, et al., *Proc. Natl. Acad. Sci. USA*, 92:8729, 1985.

Price et al., "Cellular and Molecular Biology of Alzheimer's Disease and Animal Models," Annual Reviews, vol. 45: 435–446, 1994.

Prayson et al. "The search for diagnostic criteria in Alzheimer's disease: an update," Cleveland Clinic Journal of Medicine, vol. 61: 115–122, Apr. 1994.

METHODS AND COMPOSITIONS FOR THE DETECTION OF SOLUBLE β-AMYLOID PEPTIDE

CROSS-REFERENCE TO RELATED APPLICATIONS

This is a division of application Ser. No. 08/437,067 filed May 9, 1995, now patented U.S. Pat. No. 5,593,846 and is a continuation-in-part of Ser. No. 07/911,647, filed Jul. 10, 1992, now abandoned, the disclosure of which is specifically incorporated herein by reference.

BACKGROUND OF THE INVENTION

1. Field of the Invention

The present invention relates generally to methods and compositions for detecting soluble β-amyloid peptide (βAP) in fluid samples. More particularly, the present invention relates to screening methods for the identification of inhibitors of βAP production where βAP is detected in vitro or in vivo and to diagnostic methods where βAP is detected in patient samples.

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restricted anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. βAP was first purified and a partial amino acid sequence reported in Glenner and Wong (1984) Biochem. Biophys. Res. Commun. 120:885–890. The isolation procedure and the sequence data for the first 28 amino acids are described in U.S. Pat. No. 4,666,829.

Molecular biological and protein chemical analyses conducted during the last six years have shown that βAP is a small fragment of a much larger precursor protein, referred to as the β-amyloid precursor protein (APP), that is normally produced by cells in many tissues of various animals, including humans. Knowledge of the structure of the gene encoding APP has demonstrated that βAP arises as a peptide fragment that is cleaved from APP by as-yet-unknown enzymes (proteases). The precise biochemical mechanism by which the βAP fragment is cleaved from APP and subsequently deposited as amyloid plaques in the cerebral tissue and in the walls of cerebral and meningeal blood vessels is currently unknown.

Several lines of evidence indicate that progressive cerebral deposition of βAP plays a seminal role in the pathogenesis of AD and can precede cognitive symptoms by years or decades (for review, see Selkoe (1991) Neuron 6:487). The single most important line of evidence is the discovery in 1991 that missense DNA mutations at amino acid 717 of the 770-amino acid isoform of APP can be found in affected members but not unaffected members of several families with a genetically determined (familial) form of AD (Goate et al. (1991) Nature 349:704–706; Chartier Harlan et al. (1991) Nature 353:844–846; and Murrell et al. (1991) Science 254:97–99) and is referred to as the Swedish variant. A double mutation changing lysine$^{595}$-methionine$^{596}$ to asparagine$^{595}$-leucine$^{596}$ (with reference to the 695 isoform) found in a Swedish family was reported in 1992 (Mullan et al. (1992) Nature Genet 1:345–347). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the βAP deposition disease, HCHWA-D, and a change from alanine to glycine at amino acid 692 appears to cause a phenotype that resembles AD in some patients but HCHWA-D in others. The discovery of these and other mutations in APP in genetically based cases of AD proves that alteration of APP and subsequent deposition of its βAP fragment can cause AD.

Despite the progress which has been made in understanding the underlying mechanisms of AD and other βAP-related diseases, there remains a need to develop methods and compositions for diagnosis and treatment of the disease(s). Treatment methods could advantageously be based on drugs which are capable of inhibiting the generation of βAP in vivo. To identify such drugs, it would be desirable to provide screening assays for potential drugs which can inhibit βAP generation in in vivo and in vitro models. It would be further desirable to provide methods and compositions for diagnosis of βAP-related conditions, where the diagnosis is based on detection of βAP in patient fluid samples. Specific assays for βAP detection should be capable of detecting βAP in fluid samples at very low concentrations as well as distinguishing between βAP and other fragments of APP which may be present in the sample.

2. Description of the Background Art

Glenner and Wong (1984) Biochem. Biophys. Res. Commun. 120:885–890 and U.S. Pat. No. 4,666,829, are discussed above. The '829 patent suggests the use of an antibody to the 28 amino acid βAP fragment to detect "Alzheimer's Amyloid Polypeptide" in a patient sample and diagnose AD. No data demonstrating detection or diagnosis are presented.

Numerous biochemical electron microscopic and immunochemical studies have reported that βAP is highly insoluble in physiologic solutions at normal pH. See, for example, Glenner and Wong (1984) Biochem. Biophys. Res. Commun. 122:11.31–1135; Masters et al. (1985) Proc. Natl. Acad. Sci. USA 82:4245–4249; Selkoe et al. (1986) J. Neurochem. 46:1820–1834; Joachim et al. (1988) Brain Research 474:100–111; Hilbich et al. (1991) J. Mol. Biol. 218:149–163; Barrow and Zagorski (1991) Science 253:179–182; and Burdick et al. (1992) J. Biol. Chem. 267:546–554. Furthermore, this insolubility was predicted by and is consistent with the amino acid sequence of βAP which includes a stretch of hydrophobic amino acids that constitutes part of the region that anchors the parent protein (APP) in the lipid membranes of cells. Hydrophobic, lipid-anchoring proteins such as βAP are predicted to remain associated with cellular membranes or membrane fragments and thus not be present in physiologic extracellular fluids. The aforementioned studies and many others have reported the insolubility in physiologic solution of native LAP purified from AD brain amyloid deposits or of synthetic peptides containing the βAP sequence. The extraction of βAP from cerebral amyloid deposits and its subsequent solubilization has required the use of strong, non-physiologic solvents and denaturants. Physiologic, buffered salt solutions that mimic the extracellular fluids of human tissues have uniformly failed to solubilize βAP.

Separate attempts to detect APP or fragments thereof in plasma or CSF have also been undertaken. A large secreted fragment of APP that does not contain the intact βAP region has been found in human cerebrospinal fluid (Palmert et al. (1989) Proc. Natl. Acad. Sci. USA 86:6338–6342; Weidemann et al. (1989) Cell 57:115–126; Henriksson et al. (1991) J. Neurochem. 56:1037–1042; and Palmert et al. (1990) Neurology 40:1028–1034); and plasma (Podlisny et al. (1990) Biochem. Biophys. Res. Commun. 167:1094–1101). The detection of fragments of the carboxy-terminal portion of APP in plasma has also been reported (Rumble et al. (1989) N. Engl. J. Med 320:1446–1452) as has the failure to detect such fragments (Schlossmacher et al. (1992) Neurobiol. Aging 13:421–434).

Despite the apparent insolubility of native and synthetic βAP, it has been speculated that βAP could occur in body fluids, such as cerebrospinal fluid (CSF) or plasma (Wong et al. (1985) Proc. Natl. Acad. Sci. USA 92:8729–8732; Selkoe (1986) Neurobiol. Aging 7:425–432; Pardridge et al. (1987) Biochem. Biophys. Res. Commun. 145:241–248; Joachim et al. (1989) Nature 341:226–230; Selkoe et al. (1989) Neurobiol. Aging 10:387–395).

Several attempts to measure βAP in CSF and plasma have been reported by both radioimmunoassay methods (Pardridge et al. (1987) Biochem. Biophys. Res. Commun., supra, and WO90/12870 published Nov. 1, 1990) and sandwich ELISAs (Wisniewski in *Alzheimer's Disease*, eds. Becker and Giacobini, Taylor and Francas, N.Y. pg. 206, 1990; Kim and Wisniewski in *Techniques in Diagnostic Pathology*, eds. Bullock et al., Academic Press, Boston pg. 106; and WO90/12871 published Nov. 1, 1990). While these reports detected very low levels of βAP immunoreactivity in bodily fluids, attempts to directly purify and characterize this immunoreactivity further and determine whether it represented βAP were not pursued, and the efforts were abandoned. The possibility of βAP production by cultured cells was neither considered nor demonstrated. Retrospectively, the inability to readily detect βAP in bodily fluids was likely due to the presence of amyloid precursor fragments with overlapping regions or fragments of βAP that obscured measurements and to the lack of antibodies completely specific for intact βAP. In fact, the previous findings by both Pardridge et al. and Kim et al. reported levels of βAP four-to-fivefold lower than that shown in the present invention. This is presumably because the antibodies used by both groups would crossreact with other APP fragments containing part of βAP known to be present in CSF thereby interfering with the measurement, if any, of intact βAP. The present invention overcomes these difficulties with the use of monoclonal antibodies specific to an epitope in the central junction region of intact βAP.

EP 444,856 provides a means of diagnosing Alzheimer's disease using a sandwich immunoassay to "Alzheimer's Disease Associated Protein" (ADAP). ADAP is defined as a material reactive with the monoclonal antibody termed Alz50, originally described by Wolozin et al. (1986) Science 232:648–650. Alz50 has more recently been shown to react specifically with phosphorylated forms of tau (Ksiezak-Reder et al. (1988) J. Biol. Chem. 263:7943–7947; Ueda et al. (1990) J. Neuroscience 10:3295–3304; Lee et al. (1991) Science 251:675–678). Hence, ADAPs represent phosphorylated forms of tau and are unrelated to the amyloid precursor protein of βAP described in this invention.

SUMMARY OF THE INVENTION

The present invention provides methods and compositions useful for the identification of β-amyloid peptide (βAP) production inhibitors as well as for the diagnosis and monitoring of βAP-related conditions in patients, where the methods and compositions rely on the specific detection of soluble βAP and/or βAP fragments in fluid samples. For the identification of βAP production inhibitors, a test compound is introduced to an in vitro or in vivo βAP generation model, and the effect of the test compound on the amount of soluble βAP or βAP fragment generated by the model is observed. Particularly useful as an in vitro model are cell lines which express APP variants which overproduce βAP. Test substances which affect the production of βAP and/or βAP fragments, usually by reducing the amount produced, are considered to be likely candidates for further testing for use as therapeutic drugs in the treatment of βAP-related conditions, particularly Alzheimer's Disease. For the diagnosis and monitoring of βAP-related conditions, the amount of soluble βAP and/or βAP fragments in a patient sample, such as blood, cerebrospinal fluid (CSF), urine, or peritoneal fluid, is measured and compared with a predetermined control value, such as a normal value (in the case of diagnosis) or a prior patient value (in the case of monitoring).

In a particular aspect, the present invention provides specific binding assays which are useful for the measurement of βAP concentrations in fluid samples and which may be employed in both the drug screening and patient diagnostic and monitoring methods just described. The specific binding assay of the present invention is capable of detecting soluble βAP at the very low concentrations which are characteristic of the patient fluids and conditioned culture media, typically being capable of measuring threshold concentrations in the range from about 1 ng/ml to 10 ng/ml, or lower.

Specific binding assays according to the present invention employ at least one binding substance specific for an epitope or determinant site on the βAP molecule, which site is generally not found on other fragments or degradation products of the β-amyloid precursor protein (APP). Particularly useful are antibodies which recognize a junction region within βAP, where the junction region is located about the site of normal proteolytic cleavage of APP between residues Lys$^{16}$ and Leu$^{17}$ (Esch et al. (1990) Science 248:492–495 and Anderson et al. (1991) Neuro. Science Lett. 128:126–128), typically spanning amino acid residues 13 and 28. Exemplary specific binding assays include two-site (sandwich) assays in which the capture antibody is specific for the junction region of βAP, as just described, and a labeled second antibody is specific for an epitope other than the epitope recognized by the capture antibody. Particularly useful are second antibodies which bind to the amino-terminal end of βAP, typically recognizing an epitope within amino acid residues 1–16.

In another aspect, the present invention provides a system for detecting soluble βAP in a fluid sample. The system includes a first binding substance, typically an antibody, specific for an epitope in a junction region of βAP, as described above, and a second binding substance, typically an antibody, specific for an epitope of βAP other than the epitope bound by the first binding substance. One of the first and second binding substances is bound to a solid phase, while the other is labeled, with the first binding substance preferably being a capture antibody bound to a solid phase and the second binding substance preferably being a labeled antibody, more preferably being an enzyme-labeled antibody. The system may further include substrate for the enzyme, the system is useful in performing enzyme-linked immunosorbent assays (ELISA) having high specificity and sensitivity for the detection of βAP in fluid samples.

DESCRIPTION OF THE SPECIFIC EMBODIMENTS

Figure 1:
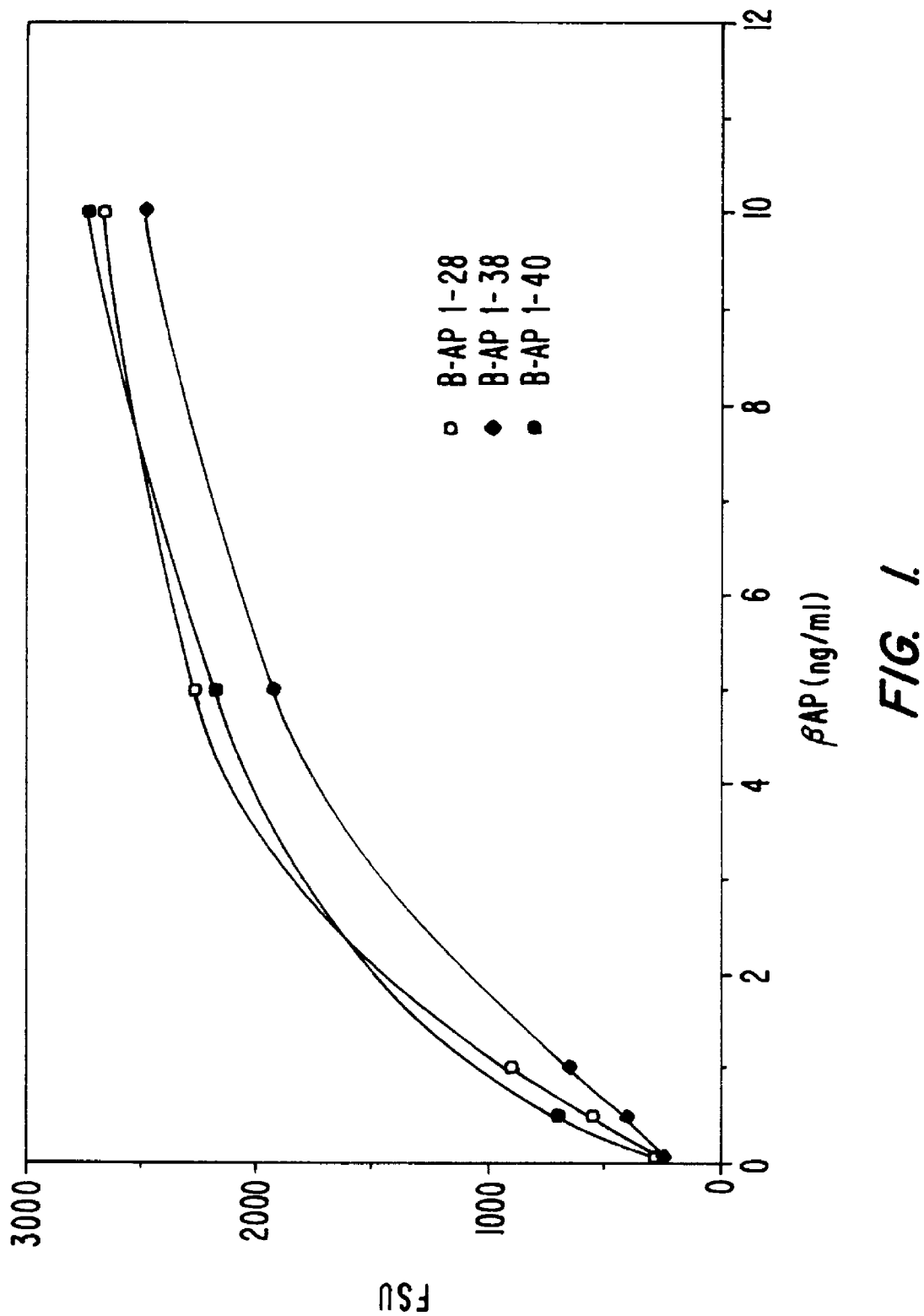
FIG. 1 is a graph illustrating the detection of three synthetic βAP peptides using an ELISA assay format with monoclonal antibody 266 as the capture antibody and monoclonal antibody 10D5 as the reporter antibody. Antibody 266 was prepared against a synthetic peptide including amino acid residues 13–28 of βAP. Antibody 10D5 was raised against a synthetic peptide including amino acid residues 1–28 of βAP.

The present invention results from the discovery that detectable amounts of soluble β-amyloid peptide (βAP) and βAP fragments are generated continuously at low concentrations by a wide variety of mammalian cells. In particular, it has been found that such βAP peptides are generated in vitro by cultured mammalian cells and may be measured in the conditioned culture medium of numerous mammalian cell lines. It has been further found that βAP peptides are present in the body fluids of various mammalian hosts, and that elevated levels of βAP peptides are associated with βAP-related conditions, such as Alzheimer's Disease and Down's Syndrome.

Based on this discovery, the present invention provides both methods for drug screening to identify potential βAP generation inhibitors and methods for diagnosing and monitoring βAP-related conditions. Both methods rely on the measurement of very low βAP concentrations in a fluid sample, typically in the range from 0.1 ng/ml to 10 ng/ml, with the present invention further providing highly sensitive and specific methods for performing such measurements. In particular, detection methods of the present invention provide for measurement of βAP at threshold concentrations of 0.1 ng/ml and below, and are sufficiently specific to distinguish βAP from other fragments of the β-amyloid precursor protein (APP) which contain precursor amino acids in addition to the 39–43 amino acids that comprise the βAP region.

The mechanism of βAP and βAP fragment generation is not presently understood. It is possible that intact or full length βAP is produced intracellularly and thereafter released or secreted into the extracellular fluid, i.e., body fluids in vivo and conditioned cell culture medium in vitro. Alternatively, it is possible that a precursor protein or fragment, which may be the entire APP or a portion thereof containing the βAP region, is secreted or released from the mammalian cells and processed outside of the cellular source. Regardless of the particular mechanism, the present invention relies on the detection and measurement of the concentrations or amounts of βAP and βAP fragments in extracellular fluids, including conditioned culture medium and body fluids, as discussed in more detail below.

The term "β-amyloid peptide (βAP) as used herein refers to an approximately 4.2 kD protein which, in the brains of AD, Down's Syndrome, HCHWA-D and some normal aged subjects, forms the subunit of the amyloid filaments comprising the senile (amyloid) plaques and the amyloid deposits in small cerebral and meningeal blood vessels (amyloid angiopathy). βAP can occur in a filamentous polymeric form (in this form, it exhibits the Congo-red and thioflavin-S dye-binding characteristics of amyloid described in connection therewith). βAP can also occur in a non-filamentous form ("preamyloid" or "amorphous" or "diffuse" deposits) in tissue, in which form no detectable birefringent staining by Congo red occurs. A portion of this protein in the insoluble form obtained from meningeal blood vessels is described in U.S. Pat. No. 4,666,829. βAP when used in connection with this invention, specifically refers to an approximately 39–43 amino acid peptide that is substantially homologous to the form of the protein produced by the method described in the patent of Glenner et al., but which, according to the instant invention, can be found in and purified from the extracellular fluid (medium) of cultured cells grown in vitro or from body fluids of humans and other mammals, including both normal individuals and individuals suffering from βAP-related conditions. Thus, βAP also refers to related βAP sequences that result from mutations in the βAP region of the normal gene. In whatever form, βAP is an approximately 39–43 amino acid fragment of a large membrane-spanning glycoprotein, referred to as the β-amyloid precursor protein (APP), encoded by a gene on the long arm of human chromosome 21. βAP is further characterized by its relative mobility in SDS-polyacrylamide gel electrophoresis or in high performance liquid chromatography (HPLC). Its 43-amino acid sequence is:

---

1

Asp Ala Glu Phe Arg His Asp Ser Gly Tyr
11

Glu Val His His Gln Lys Leu Val Phe Phe
21

Ala Glu Asp Val Gly Ser Asn Lys Gly Ala
31

Ile Ile Gly Leu Met Val Gly Gly Val Val
41

Ile Ala Thr

--- or a sequence that is substantially homologous thereto.

The term "βAP peptides" as used herein refers to intact or full length βAP as well as to fragments and degradation products of βAP which are generated at low concentrations by mammalian cells. Particular βAP fragments have a molecular weight of approximately 3 kD and are presently believed to consist of amino acid residues 11–40 and 17–40 of βAP.

The term "βAP junction region" as used herein refers to a region of βAP which is centered at the site between amino acid residues 16 and 17 ($Lys^{16}$ and $Leu^{17}$) which is a target for normal proteolytic processing of APP. Such normal processing results in a variety of APP fragments which are potentially immunologically cross-reactive with the intact βAP molecule and fragments of βAP which are to be identified in the methods of the present invention. The junction region will span amino acid residues 10 to 35, preferably spanning amino acid residues 15 to 30, with antibodies raised against a synthetic peptide consisting of amino acid residues 13–28 having been found to display the requisite specificity.

The term "β-amyloid precursor protein" (APP) as used herein is defined as a polypeptide that is encoded by a gene of the same name localized in humans on the long arm of chromosome 21 and that includes βAP within its carboxyl third. APP is a glycosylated, single-membrane-spanning protein expressed in a wide variety of cells in many mammalian tissues. Examples of specific isotypes of APP which are currently known to exist in humans are the 695-amino acid polypeptide described by Kang et al. (1987) Nature 325:733–736 which is designated as the "normal" APP; the 751-amino acid polypeptide described by Ponte et al. (1988) Nature 331:525–527 (1988) and Tanzi et al. (1988) Nature 331:528–530; and the 770-amino acid polypeptide described by Kitaguchi et al. (1988) Nature 331:530–532. Examples of specific variants of APP include point mutations which can differ in both position and phenotype (for review of known variant mutations see Hardy (1992) Nature Genet. 1:233–234).

The term "APP fragments" as used herein refers to fragments of APP other than those which consist solely of βAP or βAP fragments. That is, APP fragments will include amino acid sequences of APP in addition to those which form intact βAP or a fragment of βAP.

The term "βAP-related condition" as used herein is defined as including Alzheimer's Disease (which includes familial Alzheimer's Disease), Down's Syndrome, HCHWA-D, and advanced aging of the brain.

The terms "conditioned culture medium" and "culture medium" as used herein refer to the aqueous extracellular fluid which surrounds cells grown in tissue culture (in vitro) and which contains, among other constituents, proteins and peptides secreted by the cells.

The term "body fluid" as used herein refers to those fluids of a mammalian host which will be expected to contain measurable amounts of βAP and βAP fragments, specifically including blood, cerebrospinal fluid (CSF), urine, and peritoneal fluid. The term "blood" refers to whole blood, as well as blood plasma and serum.

According to the present invention, βAP and βAP fragments may be detected and/or measured in a variety of biological and physiological samples, including in vitro samples, such as conditioned medium from cultured cells, including transfected cell lines and endogenous cell lines, and in vivo patient samples, typically body fluids. Detection and measurement of βAP peptides may be accomplished by any technique capable of distinguishing βAP and βAP fragments from other APP fragments which might be found in the sample. Conveniently, immunological detection techniques may be employed using binding substances specific for βAP, such as antibodies, antibody fragments, recombinant antibodies, and the like, which bind with specificity and sensitivity to βAP. In particular, it has been found that antibodies which are monospecific for the junction region of βAP are capable of distinguishing βAP from other APP fragments. The junction region of βAP is centered at amino acid residues 16 and 17, typically spanning amino acid residues 13–28, and such junction-specific antibodies may be prepared using synthetic peptides having that sequence as an immunogen. Particularly suitable detection techniques include ELISA, Western blotting, radioimmunoassay, and the like.

A preferred immunoassay technique is a two-site or "sandwich" assay employing a junction-specific antibody as the capture antibody (bound to a solid phase) and a second labeled antibody which binds to an epitope other than that bound to by the capture antibody. The second labeled antibody preferably recognizes the amino terminus of βAP and may be conveniently raised against a synthetic peptide consisting essentially of amino acid residues 1–16 of βAP. Particular methods for preparing such antibodies and utilizing such antibodies in an exemplary ELISA are set forth in the Experimental section hereinafter.

Other non-immunologic techniques for detecting βAP and βAP fragments which do not require the use of βAP specific antibodies may also be employed. For example, two-dimensional gel electrophoresis may be employed to separate closely related soluble proteins present in a fluid sample. Antibodies which are cross-reactive with many fragments of APP, including βAP, may then be used to probe the gels, with the presence of βAP being identified based on its precise position on the gel. In the case of cultured cells, the cellular proteins may be metabolically labeled and separated by SDS-polyacrylamide gel electrophoresis, optionally employing immunoprecipitation as an initial separation step. A specific example of the latter approach is described in the Experimental section hereinafter.

Antibodies specific for the βAP may be prepared against a suitable antigen or hapten comprising the desired target epitope, such as the junction region consisting of amino acid residues 13–28 and the amino terminus consisting of amino acid residues 1–16. Conveniently, synthetic peptides may be prepared by conventional solid phase techniques, coupled to a suitable immunogen, and used to prepare antisera or monoclonal antibodies by conventional techniques. Suitable peptide haptens will usually comprise at least five contiguous residues within βAP and may include more than six residues.

Synthetic polypeptide haptens may be produced by the well-known Merrifield solid-phase synthesis technique in which amino acids are sequentially added to a growing chain (Merrifield (1963) J. Am. Chem. Soc. 85:2149–2156). The amino acid Sequences may be based on the sequence of βAP set forth above.

Once a sufficient quantity of polypeptide hapten has been obtained, it may be conjugated to a suitable immunogenic carrier, such as serum albumin, keyhole limpet hemocyanin, or other suitable protein carriers, as generally described in Hudson and Hay, *Practical Immunology*, Blackwell Scientific Publications, Oxford, Chapter 1.3, 1980, the disclosure of which is incorporated herein by reference. An exemplary immunogenic carrier utilized in the examples provided below is α-CD3ε antibody (Boehringer-Mannheim, Clone No. 145–2C11).

Once a sufficient quantity of the immunogen has been obtained, antibodies specific for the desired epitope may be produced by in vitro or in vivo techniques. In vitro techniques involve exposure of lymphocytes to the immunogens, while in vivo techniques require the injection of the immunogens into a suitable vertebrate host. Suitable vertebrate hosts are non-human, including mice, rats, rabbits, sheep, goats, and the like. Immunogens are injected into the animal according to a predetermined schedule, and the animals are periodically bled, with successive bleeds having improved titer and specificity. The injections may be made intramuscularly, intraperitoneally, subcutaneously, or the like, and an adjuvant, such as incomplete Freund's adjuvant, may be employed.

If desired, monoclonal antibodies can be obtained by preparing immortalized cell lines capable of producing antibodies having desired specificity. Such immortalized cell lines may be produced in a variety of ways. Conveniently, a small vertebrate, such as a mouse is hyperimmunized with the desired immunogen by the method just described. The vertebrate is then killed, usually several days after the final immunization, the spleen cells removed, and the spleen cells immortalized. The manner of immortalization is not critical. Presently, the most common technique is fusion with a myeloma cell fusion partner, as first described by Kohler and Milstein (1975) Nature 256:495–497. Other techniques including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in *Antibodies: A Laboratory Manual*, Harlow and Lane, eds., Cold Spring Harbor Laboratory, 1988, the full disclosure of which is incorporated herein by reference.

In addition to monoclonal antibodies and polyclonal antibodies (antisera), the detection techniques of the present invention will also be able to use antibody fragments, such as F(ab), Fv, $V_L$, $V_H$, and other fragments. In the use of polyclonal antibodies, however, it may be necessary to adsorb the anti-sera against the target epitopes in order to produce a monospecific antibody population. It will also be possible to employ recombinantly produced antibodies (immunoglobulins) and variations thereof as now well described in the patent and scientific literature. See, for example, EPO 8430268.0; EPO 85102665.8; EPO 85305604.2; PCT/GB 85/00392; EPO 85115311.4; PCT/US86/002269; and Japanese application 85239543, the disclosures of which are incorporated herein by reference. It would also be possible to prepare other recombinant proteins which would mimic the binding specificity of antibodies prepared as just described.

In vivo detection of βAP in patient samples can be used for diagnosing and monitoring of Alzheimer's Disease and other βAP-related conditions, such as Down's Syndrome and HCHWA-D. Suitable patient samples include body fluids, such as blood, CSF, urine, and peritoneal fluid. The presence of the βAP-related condition will generally be associated with elevated levels of βAP in the fluid when compared to those values in normal individuals, i.e., individuals not suffering from Alzheimer's Disease or any other βAP-related condition. Diagnostic concentrations of βAP in blood are in the range from 0.1 ng/ml to 10 ng/ml or higher, more generally 0.1 ng/ml to 3 ng/ml. Diagnostic concentrations of βAP in CSF are in the range from 0.1 ng/ml to 25 ng/ml or higher, more generally 0.1 ng/ml to 5 ng/ml.

In addition to initial diagnosis of the βAP-related condition, the measured concentrations of βAP may be monitored in order to follow the progress of the disease, and potentially follow the effectiveness of treatment (when such treatments become available). It would be expected that levels of βAP would decrease with an effective treatment regimen.

In vitro monitoring of βAP levels in conditioned culture medium from a suitable cell culture may be used for drug screening. By growing cells under conditions which result in the accumulation of βAP in the conditioned culture medium, and exposing the cultured cells to test compounds, the effect of these test compounds on βAP production may be observed. It would be expected that test compounds which are able to diminish the amount of βAP accumulation would be candidates for testing as inhibitors of βAP generation. Suitable cell lines include human and animal cell lines, such as the 293 human kidney cell line, human neuroglioma cell lines, human HeLa cells, primary human endothelial cells (e.g. HUVEC cells), primary human fibroblasts or lymphoblasts, primary human mixed brain cells (including neurons, astrocytes, and neuroglia), Chinese hamster ovary (CHO) cells, and the like.

Preferred for use in drug screening methods according to the present invention are cell lines capable of expressing APP variants which overproduce βAP. By "overproduce," it is meant that the amount of βAP produced from the variant APP will be greater than the amount produced from any or all of the normal APP isoforms, e.g., the 695, 751, and 770 amino acid isoforms which have been previously described. Particularly preferred are APP variants having one or several amino acid substitutions directly amino-terminal of the βAP cleavage site. For example, as shown in the Experimental section herein, K293 cells which express an APP DNA bearing a double mutation ($Lys^{595} \rightarrow Asn^{595}$ and $Met^{596} \rightarrow Leu^{596}$) found in a Swedish FAD family produce approximately six-to-eightfold more βAP than cells expressing normal APP. The mutation at residue 596 appears to be principally responsible for the increase.

Similarly, in vivo monitoring of βAP in animal models, such as the mouse animal model disclosed in WO 91/19810, the disclosure of which is incorporated herein by reference, and animal models expressing other APP isotypes and/or variants, may also be used to screen compounds for therapeutic effectiveness (usually for testing of compounds which have previously been identified by an in vitro screen, such as the in vitro screen described above). The test compound (s) are administered to the animal and the level of βAP or βAP fragment in a body fluid observed. Test compounds which reduce the level of the βAP in certain body fluids are considered to be candidates for further evaluation.

The test compounds can be any molecule, compound, or other substance which can be added to the cell culture without substantially interfering with cell viability. Suitable test compounds may be small molecules, biological polymers, such as polypeptides, polysaccharides, polynucleotides, and the like. The test compounds will typically be administered to the culture medium at a concentration in the range from about 1 nM to 1 mM, usually from about 10 μM to 1 mM. Test compounds which are able to inhibit generation, accumulation, or secretion of βAP are considered as candidates for further determinations of the ability to decrease βAP production in cells and/or animals.

The present invention further comprises methods for inhibiting β-amyloid production in cells, where the method includes administering to the cells compounds selected by the method described above. The compounds may be added to cell culture in order to inhibit βAP production by the cultured cells. The compounds may also be administered to a patient in order to inhibit the deposition of amyloid plaque associated with Alzheimer's and other βAP-related diseases.

The present invention further comprises pharmaceutical compositions incorporating a compound selected by the above-described method and including a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosure of which is incorporated herein by reference.

The pharmaceutical compositions just described are suitable for systemic administration to the host, including both parenteral, topical, and oral administration. The pharmaceutical compositions may be administered parenterally, i.e. subcutaneously, intramuscularly, or intravenously. Thus, the present invention provides compositions for administration to a host, where the compositions comprise a pharmaceutically acceptable solution of the identified compound in an acceptable carrier, as described above.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intraarterial infusion of hypertonic solutions which can transiently open the blood-brain barrier.

The concentration of the compound in the pharmaceutical carrier may vary widely, i.e. from less than about 0.1% by weight of the pharmaceutical composition to about 20% by weight, or greater. Typical pharmaceutical composition for intramuscular injection would be made up to contain, for example, one to four ml of sterile buffered water and one μg to one mg of the compound identified by the method of the present invention. The typical composition for intravenous infusion could be made up to contain 100 to 500 ml of sterile Ringer's solution and about 1 to 100 mg of the compound.

The pharmaceutical compositions of the present invention can be administered for prophylactic and/or therapeutic treatment of diseases related to the deposition of βAP, such as Alzheimer's disease, Down's syndrome, and advanced aging of the brain. In therapeutic applications, the pharmaceutical compositions are administered to a host already suffering from the disease. The pharmaceutical compositions will be administered in an amount sufficient to inhibit further deposition of βAP plaque. An amount adequate to accomplish this is defined as a "therapeutically effective dose." Such effective dose will depend on the extent of the disease, the size of the host, and the like, but will generally range from about 0.01 μg to 10 mg of the compound per kilogram of body weight of the host, with dosages of 0.1 μg to 1 mg/kg being more commonly employed.

For prophylactic applications, the pharmaceutical compositions of the present invention are administered to a host susceptible to the βAP-related disease, but not already suffering from such disease. Such hosts may be identified by genetic screening and clinical analysis, as described in the medical literature (e.g. Goate (1991) Nature 349:704–706). The pharmaceutical compositions will be able to inhibit or prevent deposition of the βAP plaque at a symptomatically early stage, preferably preventing even the initial stages of the β-amyloid disease. The amount of the compound required for such prophylactic treatment, referred to as a prophylactically-effective dosage, is generally the same as described above for therapeutic treatment.

The following examples are offered by way of illustration, not by way of limitation.

EXPERIMENTAL

Materials and Methods

1. Antibody Preparation.

a. Monoclonal Antibodies to the βAP Junction Region.

Monoclonal antibodies to the junction region of βAP were prepared using a synthetic peptide spanning amino acid residues 13–28 ($\beta AP_{13-28}$). $\beta AP_{13-28}$ was conjugated to an immunogen (α-CD3ε antibody; Clone No. 145–2C11, Boehringer-Mannheim) using m-maleimidobenzoyl-N-hydroxysuccinimide ester (MBS) according to the manufacturer's (Pierce) instructions.

A/J mice were immunized initially intraperitoneally (IP) with the βAP conjugate mixed with complete Freund's adjuvant. Fourteen days later, the mice were boosted IP with the βAP conjugate mixed with phosphate buffered saline (PBS) at 14 day intervals. After six total boosts, the mice were finally boosted intravenously with βAP conjugate mixed with PBS and fused 3 days later. Fusion of spleen cells with P3.653 myeloma cells was performed according as described in Oi and Herzenberg, *Selective Methods in Cellular Immunology,* Mishell and Shigii, Eds., W. H. Freeman and Company, San Francisco, Chapter 17 (1980). Serum titers and initial screens were performed by the RIA method described below. Several clones were expanded to a 24 well plate and subjected to further analysis as described below. Clones of interest were produced in mouse ascites.

The RIA method used to screen serum bleeds and fusion hybridoma supernatants was based upon a method developed by Wang et. al. (1977) J. Immunol. Methods 18:157–164. Briefly, the supernatant (or serum) was incubated overnight at room temperature on a rotator with $^{125}$I-labeled $\beta AP_{1-28}$ and Sepharose® 4B beads to which sheep anti-mouse IgG had been coupled via cyanogen bromide. The beads from each well were harvested onto glass fiber filter discs with a cell harvester and washed several times with PBS. The filter discs were then transferred to gamma tubes and the bound radioactivity was counted in a gamma counter.

All hybridomas were tested for binding to $\beta AP_{1-28}$ using the method described above in the initial screen, and then retested 3 days later. $\beta AP_{1-28}$ positive clones were further characterized for reactivity to $^{125}$I-labeled $\beta AP_{1-16}$ using the RIA method described above. No clones were found to bind $\beta AP_{1-16}$. In a peptide capture ELISA, all clones were found to react with $\beta AP_{13-28}$ while no clones reacted to $\beta AP_{17-28}$. Therefore, it was determined that all clones; had an epitope within the junction region spanning amino acids 16 and 17.

Based on results of the above assays, several clones were expanded into 24 well plates. These clones were further characterized by saturation analysis. Supernatants at the 50% titer point (as determined by the RIA method described above) were added to wells containing Sepharose®-sheep anti-mouse IgG beads, a constant amount of $^{125}$I-labeled $\beta AP_{1-28}$, and varying amounts of unlabeled $\beta AP_{13-28}$ or $\beta AP_{17-28}$. The concentration of cold peptide for 50% inhibition was determined for each antibody. For the $\beta AP_{17-28}$, no inhibition was seen at 100 ng/well for any clones. The 50% inhibition point for $\beta AP_{13-28}$ ranged from 10–80 ng/well. The clones were also characterized based on reactivity in Western blots. Based on titer point, sensitivity (as determined by the 50% inhibition point), and reactivity on Western blot, several clones were produced in ascites.

Antibodies from hybridomas designated 067, 266, 297, and 361 were selected for use as a capture antibody in the assays described below.

b. Monoclonal Antibodies to the N-terminal Region of $\beta AP$.

Monoclonal antibodies to the N-terminal region of $\beta AP$ were prepared using a synthetic peptide spanning amino acid residues 1–28 ($\beta AP_{1-28}$) $\beta AP_{1-28}$ was chemically coupled using disuccimidyl suberate (DSS) to rabbit serum albumin (RSA) using a 20:1 molar ratio of peptide to protein in 50 mM sodium phosphate, pH 7.0, 150 mM NaCl, overnight at 21° C. using 1 mM DSS (Hyman et al. (1992) J. Neuropath. Exp. Neuro. 51:76).

Antibodies 10D5 and 6C6 were obtained from a fusion where mice had received 5 injections of $\beta AP_{1-28}$ coupled to RSA via DSS at 100 µg/ml. The initial injection was in complete Freund's adjuvant (CFA) followed by second and subsequent injections in incomplete Fruend's adjuvant (IFA) every 10–14 days. Three days before the fusion, mouse 4 which had a titer of 1/70,000 as measured by ELISA against $\beta AP_{1-28}$, received 100 µg of $\beta AP_{1-28}$ RSA in PBS intraperitoneally as a final boost. Screening was done by ELISA and on paraffin-fixed AD brain sections. The coating concentration of $\beta AP_{1-28}$ was 1 µg/well. 10D5 and 6C6 were positive by ELISA and AD brain tissue section.

Antibodies from hybridomas designated 10D5 and 6C6 were selected for use as a reporter antibody in the assays described below.

c. Polyclonal Antibodies.

Polyclonal antibodies were raised against synthetic peptices $\beta AP_{1-38}$, $\beta AP_{1-40}$, and $\beta AP_{1-42}$, and were designated anti-$\beta AP_{1-38}$ (antiserum Y), anti-$\beta AP_{-40}$ (antiserum 1280) and anti-$\beta AP_{1-42}$ (antiserum HM). Rabbits were immunized with 0.5–3.0 mg of one of these peptides (unconjugated) in complete Freund's adjuvant intradermally. The rabbits received booster injections of 0.1–0.5 mg peptide 3 weeks after primary immunization and at approximately 2–4 week intervals thereafter until high titers of anti-peptide reactivity could be detected in samples of the rabbit serum. These antisera were then used in immunological assays at dilutions ranging from 1:300 to 1:1,500.

2. ELISA Assay.

a. Binding of Capture Antibody to Microtiter Wells.

Monoclonal antibody 266 was diluted to a concentration of 5 µg/ml, and monoclonal antibody 067 to 10 µg/ml in a buffer containing $NaH_2PO_4.7H_2O$, 26.2 g/L; $NaN_3$, 1 g/L; pH 8.3. One hundred µl/well of this solution was then dispensed in a 96 well polystyrene transparent COSTAR plate and incubated overnight at room temperature. Following coating, the remaining solution was aspirated and the non-specific antibody binding sites were blocked with 0.25% human serum albumin (HSA) dissolved in a buffer containing $NaH_2PO_4.H_2O$, 1 g/L; $Na_2HPO_4.7H_2O$, 10.8 g/L; $NaN_3$, 0.5 g/L and sucrose, 25 g/L; pH 7.4. These coated/blocked plates were used immediately or dried in a desiccator and stored in a dry container at 4° C. for a maximum of 5 days.

b. Assay Protocol.

Calibrators containing known amounts of $\beta AP$ and samples from various bodily or extra bodily fluids were then added to the plate at 100 µl/well. The samples were added undiluted or diluted in a buffer containing $NaH_2PO_4.H_2O$, 0.2 g/L; $Na_2HPO_4.7H_2O$, 2.16 g/L; $NaN_3$, 0.5 g/L; BSA (globulin free) 6 g/L; Triton X-405, 0.5 mL/L; NaCl, 8.5 g/L; pH 7.4. Samples and calibrators were incubated in the wells for 1 hour at room temperature, subsequently aspirated, and the wells washed with 300 µl/well of a solution containing NaCl, 80 g/L; KCl, 3.8 g/L; Tris base, 5.85 g/L; Tris HCl, 31.75 g/L; and 0.05% Tween® 20; pH 7.5 (TBS).

NHS-biotin (15 mg) was dissolved in 0.25 ml dimethylsulfoxide, and 10 µl of this solution was added to 1 mg of 10D5 or 6C6 antibody suspended in 1 ml of sodium carbonate solution, 50 mM, pH 8.5. The mixture was incubated in the dark for 1½ hours at room temperature and then dialyzed against phosphate buffered saline, pH 7.4 for 48 hours at 4° C., to produce biotinylated reporter antibody. One hundred µl/well of the biotinylated reporter antibody (10D5 or 6C6) diluted to 3 µg/ml was then added to each well and incubated for another hour at room temperature. The antibody diluent consisted of Trizma base, 1.21 g/L; NaCl, 29.22 g/L; $NaN_3$, 1.5 g/L, Triton X 405, 0.5 ml/L; PEG (Mw 3350), 40 g/L; Mg $Cl_2.6H_2O$, 0.095 g/L; $ZnCl_2$, 0.014 g/L; fetal bovine serum 100 ml/L; and BSA 2.5 g/L, pH 7.4.

After 1 hour incubation at room temperature with the reporter antibody (10D5 or 6C6) the supernatant was aspirated and the wells were washed three times with 300 µl/well of TBS. Streptavidin alkaline phosphatase (100 µl/well, diluted 1:2000 in the conjugate diluent buffer) was added and incubated for another hour at room temperature. The supernatant was then aspirated and washed 3 times with 300 µl/well TBS. Fluorescent substrate (4-methyl-umbellipheryl phosphate in 2-amino-2-methyl propranolol buffer; pH 9.5; (100 µl/well) was added) and fluorescence read and expressed as relative fluorescent units (FSU) after 15 minutes using a Cytofluor 2300 from Millipore, with 360/40 excitation filter and 460/40 emission filter.

3. Cultured Cells.

Human cells (and cells from other mammals) were cultured under standard cell culture conditions in plastic dishes or multi-well microtiter plates. In particular, human embryonal kidney carcinoma 293 cells (hereinafter designated K293 cells) were grown in Dulbecco's modified Eagle's medium (DMEM) containing 10% fetal calf serum and antibiotics. K293 cells that had previously been transfected with a recombinant DNA construct containing the full coding region of the β amyloid precursor protein (APP) were utilized in addition to untransfected K293 cells (Selkoe et al. (1988) Proc. Acad. Sci. USA 85:7341–7345; and Oltersdorf et al. (1990) J. Biol. Chem. 265:4492–4497). The transfected cells express high levels of the APP protein, compared to the usual background levels of endogenous APP characteristic of K293 cells.

Several other cell types were also cultured, including human umbilical vein endothelial cells (HUVEC); a human megakaryocytoid leukemic cell line designated DAMI; Chinese hamster ovary (CHO) cells, primary human fibroblasts, and primary mixed brain cell cultures (including neurons, astrocytes, and microglia) established from human or rodent brain.

These various cell lines were grown at 37° C. in a tissue culture incubator containing an atmosphere of 95% oxygen and 5% carbon dioxide. The cells were routinely subcultured by providing fresh culture medium at regular intervals. The extracellular fluid surrounding the cells (conditioned medium) was harvested from cells grown either under standard resting conditions or following various biochemical treatments of the cells. All cultured cells and their derived media samples were handled under aseptic conditions.

Cultures of human-mixed brain cells for use in immunoaffinity chromatography studies were prepared as follows. Fetal neural tissue specimens were obtained from 12–14 week old fetal cadavers. Samples of cerebral cortex were rinsed twice with Hank's Balanced Saline solution (HBSS). Cortical tissue (2–3 grams) was placed in 10 mls of cold HBSS to which 1 mg of DNase (Sigma Chemical Co., St. Louis, Mo. D3427) was added. The triturated suspension was filtered through Nitex nylon screens of 210 μm then 130 μm, as described by Pulliam et al. (1984) J. Virol. Met. 9:301.

Cells were harvested by centrifugation and resuspended in neuronal medium (MEM fortified with 10% fetal bovine serum, 1% glucose, 1 mM Na pyruvate, 1 mM glutamine, 20 mM KCl). Polyethyleneimine coated 100 mm dishes were seeded with $1.5 \times 10^7$ cells in 8 mls of neuronal medium. The medium was harvested and fresh medium added twice weekly. The conditioned medium from the cells (HFBC-CM) was frozen until use.

4. Immunoprecipitation/Autoradiography Assay for βAP.

a. Metabolic Labeling and Immunoprecipitation.

K293 cells grown under standard culture conditions underwent metabolic labeling of newly synthesized proteins by addition of $^{35}$S-radiolabeled methionine to the culture medium. During this step, the medium contained no unlabeled ("cold") methionine but was otherwise identical to the standard medium used to culture K293 cells. Amounts of radioactive methionine varying from 50–300 pCi/ml of media were used in the labeling experiments. Cells were incubated for approximately 10–20 hours. Thereafter, the medium containing any radiolabeled proteins released from the cell was collected.

A polyclonal antibody produced to a synthetic βAP peptide comprising the amino acids Asp-1 through Val-40 ($\beta AP_{1-40}$) was added to the collected media and incubated for periods varying from 2–10 hours. This allowed antigen-antibody complexes to form between the anti-βAP antibody and any βAP peptide present in the culture media. Thereafter, a protein A-Sepharose® reagent capable of binding to immunoglobulins (antibodies) was added, and this mixture was further incubated for varying periods of 2–10 hours. This incubation enabled the protein A-Sepharose® beads to bind to the anti-βAP antibodies which in turn were bound to βAP peptide. The conditioned media was then centrifuged at 12,000×g for 10 minutes to pellet the antigen-antibody-protein A-Sepharose® bead complexes.

b. SDS-Polyacrylamide Gel Electrophoresis (PAGE) of the Immunoprecipitate.

The immunoprecipitates of the media from metabolically labeled cells was electrophoresed on 10–20% Tris-tricine gels, which have the advantage of resolving low molecular weight proteins (such as βAP) well. The gels were then dried and exposed to X-ray film to produce an autoradiogram or fluorogram. Exposure times varied but were usually in the range of 2–7 days. Following development of the X-ray film, any radiolabeled proteins that were precipitated from the cell media by the anti-βAP antibody were visualized as dark bands at the appropriate molecular weight (i.e., 4 kD).

5. Preparation of 266 Resin.

Antibody 266 (15 mls at 0.85 mg/ml) was dialyzed versus 10 mM Na acetate, 15 mm NaCl, pH 5.5 and then coupled to Affi-Gel® Hz Hydrazide (Bio-Rad, Richmond, Calif.) according to the manufacturer's protocol, using approximately 5 mls of resin. One ml of the resin was placed in a 1×10 cm column for the purification of βAP from 4 liters of conditioned medium.

6. Western Blotting.

Samples were subjected to SDS-PAGE on 10%–20% Tricine gels (Novex) and transferred to PVDF membranes (Pro-blot, Applied Biosystems) at 40 volts, overnight, in the buffer system described by Towbin, et al. (1979) Proc. Natl. Acad. Sci. USA 76:4350–4354. Visualization of immunoreactive proteins employed the TROPIX chemiluminescence system according to the manufacturer's directions for the AMPPD substrate. The primary antibody used was 10D5 at a concentration of 5 μg/ml.

7. Construction and Analysis of the 'Swedish' FAD Mutation.

The Swedish mutation involves two adjacent base pair conversions: nucleotide 1785 G to T and nucleotide 1786 A to C which Leads to two amino acid exchanges: Lys→Asn$^{595}$ and Met→Leu$^{596}$ (all numbering based on APP$_{695}$).

To analyze the biochemical effect of this mutation on the metabolism of APP in vitro it was introduced by in vitro mutagenesis in an expression vector for eukaryotic expression of APP molecules (described in Selkoe et al., 1988 supra). In this case, both forms of the vector carrying the 695 and the 751 amino acid forms of APP were used. Mutagenesis was performed by use of two oligonucleotide primers derived from the APP sequence and polymerase chain reaction (PCR). Primer 1 (sense) is a 30-mer and has the sequence GAG GAG ATC TCT GAA GTG AAT CTG GAT GCA. This primer contains a BglII restriction endonuclease site (AGA TCT) corresponding to the BglII site in position 1770 of APP and contains the two described nucleotide exchanges at positions 24 and 25 of the primer. Primer 2 (anti-sense) is a 29-mer with the sequence AAT CTA TTC ATG CAC TAG TTT GAT ACA GC. The primer contains a SpeI restriction endonuclease site (ACT AGT) corresponding to position 2360 of APP. Using a normal APP cDNA for a template, the two primers allow the creation of a DNA fragment of approximately 600 basepairs in length by standard PCR (reagents and protocols from Perkin Elmer). The obtained fragment as well as the expression vector containing the normal APP cDNA were cleaved with restriction endonucleases BglII and SpeI.

BglII and SpeI were chosen as they are both single cut sites in this vector and therefore allow the simple removal of the non-mutated restriction fragment corresponding to the fragment created by PCR. Accordingly the approximately 600 basepair vector fragment was replaced by the PCR generated fragment of equal length carrying the mutation by standard techniques. DNA of recombinant bacterial clones was obtained by standard methods which was screened for the absence of an Mbo II restriction endonuclease site. Then the DNA sequence was confirmed by sequencing of the complete region that had undergone the PCR reaction.

In addition to the construction of the double mutation, the effects of each of the two mutations were separately examined. Using appropriate primers or olignucleotides specific for either the 595 Lys→Asn substitution or the 596 Met→Leu substitution, DNA constructs were prepared and used to transfect K293 cells as described.

Analysis of the effects of the mutation was carried out by transient expression of the obtained mutated clone in 293 cells. The DOTAP reagent transfection method was used according to the manufacturer's specifications (Boehringer Mannheim, Indianapolis, Ind.). Conditioned medium was harvested 48 hours after transfection. Transfection efficiency was assessed by a sandwich ELISA for APPs in the conditioned medium with affinity purified polyclonal antibodies B5 (biotinylated) to a bacterial fusion protein of $APP_{444-592}$ and the capture antibody B3, to a bacterial fusion protein of $APP_{20-304}$. βAP levels were measured by the ELISA described above in Example 2. As described below, the measurement of βAP in the conditioned media of transiently transfected K293 cells expressing the Swedish variant form of APP shows a 6–7 fold increase in production of βAP.

Results

The βAP ELISA assay was used to detect known amounts of synthetic βAP peptides $βAP_{1-38}$ and $βAP_{1-40}$. The assay employing 266 capture antibody and 10D5 reporter antibody was able to detect the peptides at 0.1 ng/ml. See FIG. 1. Moreover, the 266/10D5 assay was found not to significantly cross-react with full length APP, secreted APP 695 or 751, recombinant APP fragments constructs 15 or 6, βAP fragments 15–20, 11–18, 13–18, or 13–20, or fibrinogen (Table I).

TABLE I

βAP Cross-Reactivity in 266/10D5 ELISA

| Molecule | ng/ml | % Cross-Reactivity |
|---|---|---|
| Full Length APP | 1-100 | 0 |
| Secreted APP 695 | 1-100 | 0 |
| Secreted APP 751 | 1-100 | 0 |
| Construct 15* | 1-100 | 0 |
| Construct 6** | 1-100 | <0.1 |
| βAP Fragment 15–20 | 1-1000 | 0 |
| βAP Fragment 11–18 | 1-1000 | 0 |
| βAP Fragment 13–18 | 1-1000 | 0 |
| βAP Fragment 13–20 | 1-1000 | 0.2 |
| Fibrinogen Type I | 1-1000 | 0 |
| Fibrinogen Type II | 1-1000 | 0 |
| Fibrinogen Type III | 1-1000 | 0 |

*Described in Sinha et al. (1991) J. Biol. Chem. 266:2104–21013.
**Residues 590–695, as numbered in 695 isoform.

The ELISA assay was used to screen blood and CSF samples from humans, dogs, guinea pigs, and rats. Detectable amounts of βAP were found, with concentrations in the ranges set forth in Table II.

TABLE II

βAP Level in Plasma and CSF of Various Species

| Species | CSP βAP (ng/ml) | Plasma βAP (ng/ml) |
|---|---|---|
| Human | 0.1–20.0 | 0.1–30.0 |
| Dog | 2.0–10.0 | 2.0 |
| Guinea Pig | 2.5–8.0 | 4.0–5.0 |
| Rat | 1.5 | ND |
| Rabbit | 1.5–9.0 | 0.5–3.0 |

Figure 2A:
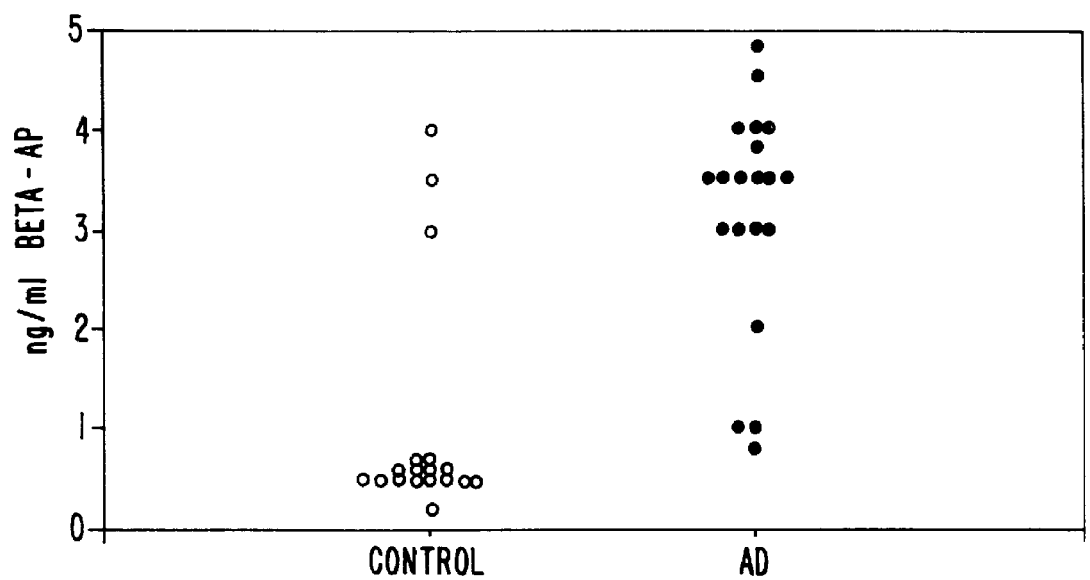
FIGS. 2A and 2B are charts comparing the plasma and CSF concentrations of βAP in normal control and AD patients.
Figure 2B:
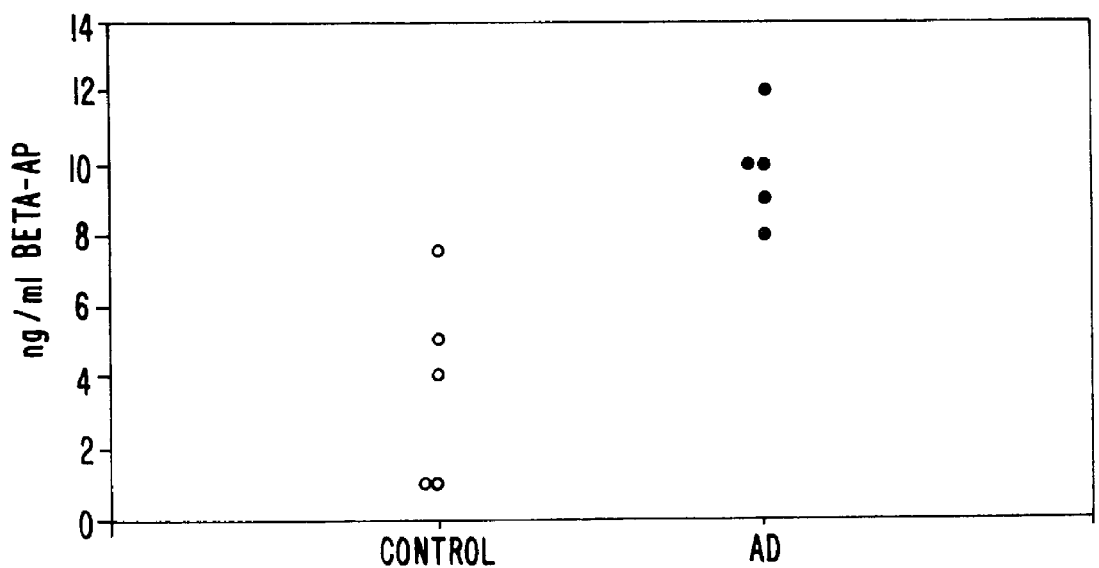
Figure 3:
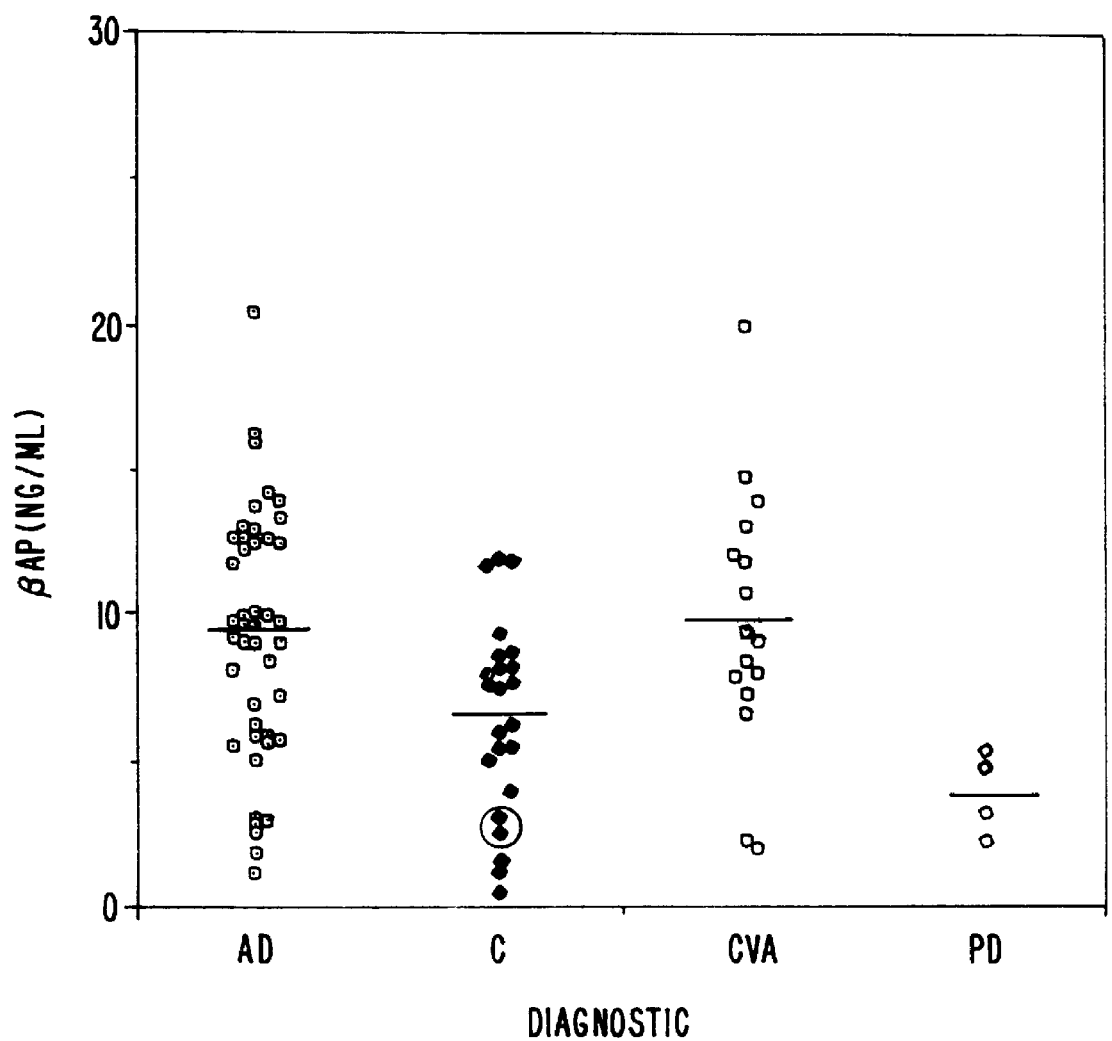
FIG. 3 is a chart comparing the CSF concentration of βAP in normal controls (C), Alzheimer's Disease patients (AD), cerebral vascular accident (CVA) patients (stroke), and Parkinson's Disease (PD) patients.

A comparative study was carried out in groups of normal individuals and AD patients, both in plasma and CSF. Samples were screened using the ELISA assay, with the results for plasma set forth in FIG. 2A and the results for CSF set forth in FIG. 2B. βAP levels in CSF for normal individuals (C), AD patients, cerebrovascular accident (CVA), and Parkinson's Disease (PD) are set forth in FIG. 3. A CSF pool of approximately 1000 individuals had a mean value of 2.5 ng/ml in CSF, circled in FIG. 3, row C. The rest of the control individuals had a variety of non-AD neuronal degenerative diseases. The AD mean values are well above the control pool value.

A number of transfected and non-transfected cultured cells were tested for release of βAP using the ELISA assay. All cells tested were found to release βAP into the culture medium, with the APP transfected cells releasing higher concentrations than released from non-transfected cultured cells, as set forth in Table III.

TABLE III

Release of βAP by Cells in Culture

| Cell Type | Transfection | βAP (ng/ml) |
|---|---|---|
| K293 | — | 0.1–0.4 |
| K293 | 695 | 1.6–2.5 |
| K293 | 751 | 1.2–2.5 |
| Mixed brain cells | — | 4.0 |
| CHO | 751 | 2.0–9.0 |

Figure 6:
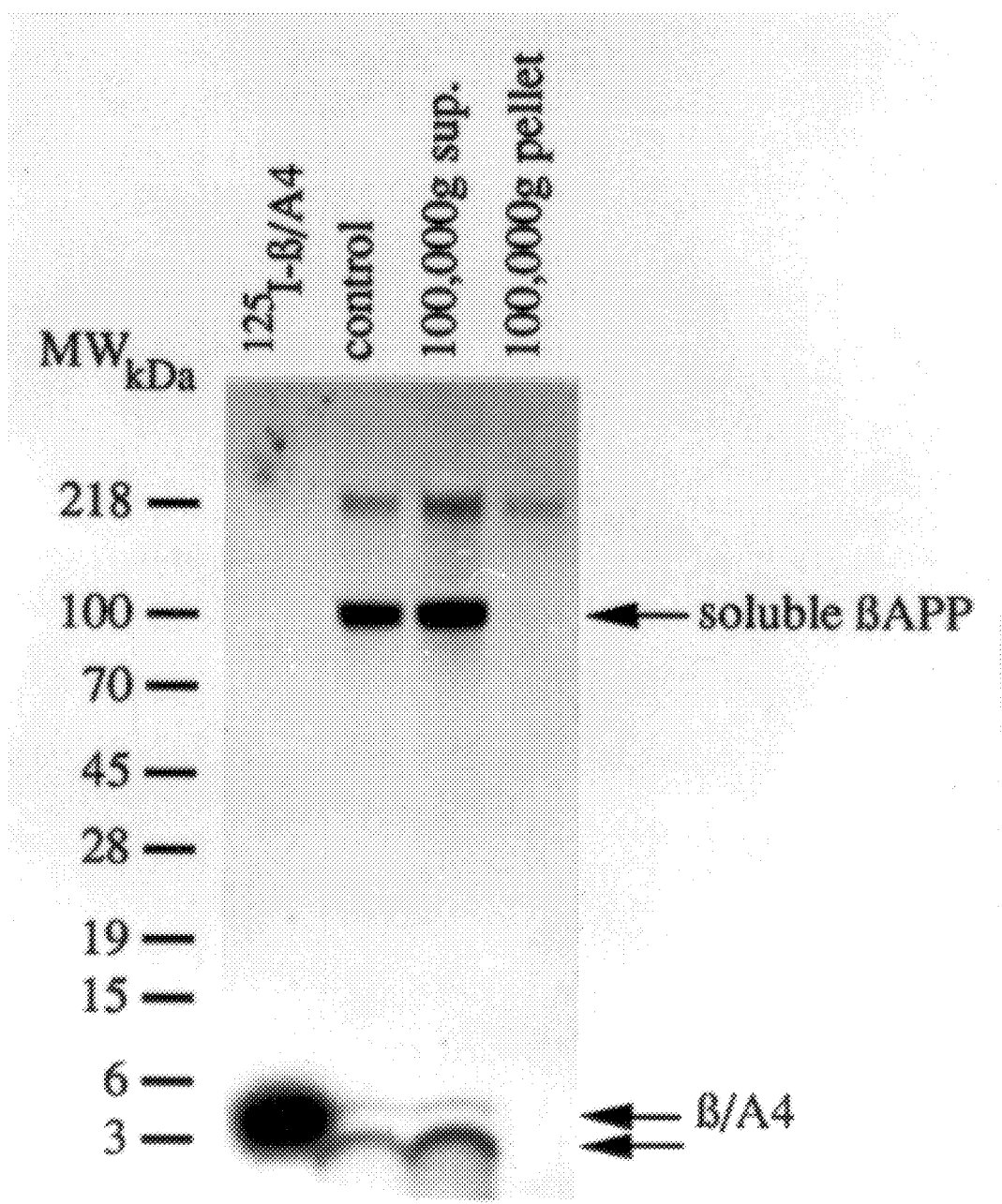
FIG. 6 is an autoradiogram demonstrating that βAP in the media of human kidney 293 cells is fully soluble and that it remains in the post-$10^5$×g supernatant and is not found in the post-$10^5$×g pellet after ultracentrifugation.

Using the immunoprecipitation/autoradiography assay described above in Example 4, it was shown that polyclonal antibody 1280 immunoprecipitated a 4 kD protein from K293 cell media that comigrated precisely with a standard sample of radioiodinated synthetic $βAP_{1-40}$ peptide. In addition, a 3 kD protein was simultaneously precipitated. This appears to be a fragment of βAP lacking the first 10 or 16 amino acids. When the 1280 antibody was preabsorbed with synthetic $βAP_{-40}$ peptide to block its activity, no 3 kD or 4 kD bands were precipitated from the K293 cell media. When the conditioned medium of K293 cells overexpressing APP was centrifuged at 100,000×g for 2 hours (to pellet any insoluble proteinaceous material), immunoprecipitation/autoradiography with the 1280 antibody showed that substantially all of the 3 kD and 4 kD proteins remained in the supernatant, (see FIG. 6). This experiment demonstrates the βAP found in culture media is a soluble molecule, in contrast to previous reports about βAP in postmortem human brain tissue (see for example, Glenner and Wong (1984), supra).

The precipitation of the 4 kD βAP comigrating peptide from the media of K293 cells transfected with βAPP cDNA was confirmed by utilizing additional βAP antibodies. Antibody Y to synthetic βAP$_{1-38}$ peptide precipitated the 4 kD protein in identical fashion to antibody 1280. Also, antibody HM to synthetic βAP$_{1-42}$ precipitated the 4 kD protein. As a control, each of these antibodies was preabsorbed with its synthetic peptide antigen, thereby neutralizing its activity. Thereafter, the antibodies no longer immunoprecipitated the 4 kD βAP peptide from conditioned media. As an additional control, the preimmune sera (i.e., a sample of normal serum taken from each rabbit used to raise the polyclonal antibodies prior to the actual immunization) did not immunoprecipitate the 4 kD peptide from the media.

To ascertain the immunochemical specificity of the 4 kD βAP comigrating peptide precipitated from media, other antibodies to regions of APP flanking the βAP region were used in the above immunoprecipitation/autoradiography assay. For example, an antibody to the 20-amino acid region immediately amino-terminal to the beginning of the βAP region of APP failed to precipitate the 4 kD peptide from media. Likewise, an antibody to the last 20 amino acids at the carboxyl terminus of APP (60 amino acids beyond the βAP region) also failed to precipitate the 4 kD peptide. In contrast, an antibody to the first 15 residues of βAP successfully precipitated the 4 kD band. Likewise, antibodies to the middle portion of βAP also precipitated the 4 kD peptide, but not the 3 kD peptide discussed above. These various antibody precipitations demonstrate that the 4 kD peptide present in the media of cultured cells (e.g., K293 cells) shows the specific immunochemical reactivities characteristic of βAP. The 3 kD peptide in the media shows the specific immunochemical reactivity of βAP lacking the first 10 or 16 residues. Evidence that the antibodies were active in each reaction was provided by the co-precipitation from the same media of the normal secreted fragment of APP (designated "soluble APP" or "APP$_s$") whenever the precipitation reactions were carried out with antibodies to that region of APP. This large soluble APP fragment is known to be present normally in the media of cultured cells expressing APP. Its coprecipitation by anti-βAP antibodies thus represents a positive control reaction demonstrating the intact activity of the antibodies used in this assay.

Figure 5:
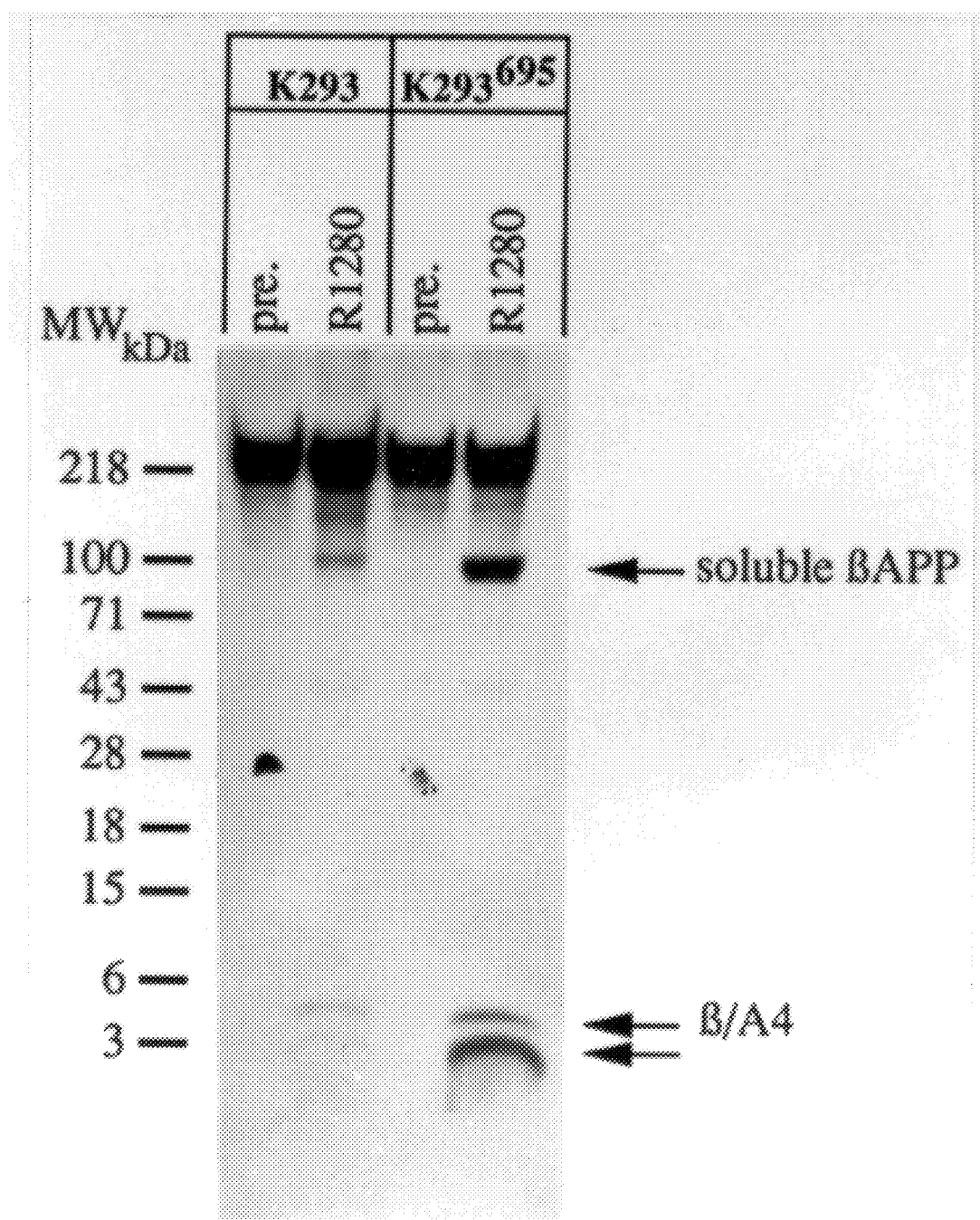
FIG. 5 is an autoradiogram demonstrating the presence of soluble βAP in the culture fluid of human kidney 293 cells. The βAP was immunoprecipitated from the culture fluid with a βAP-specific antibody to residues 1–40 of βAP.

As an additional control reaction to demonstrate that the immunoprecipitated 4 kD protein comigrating with synthetic βAP indeed represented authentic βAP, the media of cells transfected with an APP cDNA (and thus overexpressing APP) were compared to the media of untransfected cells. Immunoprecipitation/autoradiography showed an increased amount of precipitable 4 kD protein in the media of the transfected versus non-transfected cells, as expected from their increased production of the APP precursor molecule. See FIG. 5. Similarly, the media of the transfected cells showed more of the APP 3 soluble fragment of APP than the media of the non-transfected cells; this positive control reaction was observed simultaneously in the immunoprecipitates that contained the 4 kD protein.

The same result was obtained when a different cell type, chinese hamster ovary (CHO) cells, was used. Comparison of CHO cells either untransfected or transfected with APP cDNA showed increased levels of the 4 kD 1280-precipitable peptide in the media of the latter cells. These results provided further evidence that the 4 kD protein in the cell media was bona fide βAP.

Authentic, native βAP was extracted from autopsied human cerebral cortex of patients who died with AD. This sample of Aβ from AD brain tissue comigrated with the 4 kD 1280-precipitable peptide from cultured cell media when analyzed by SDS-polyacrylamide gel electrophoresis. This comigration provided further support for the identity of the 4 kD peptide as βAP.

Four liters of human fetal brain culture-conditioned media (HFBC-CM) were thawed and filtered through a 0.45 μm filtering flask. Leupeptin (1 μg/ml) and PMSF (35 μg/ml) taken from a 35 mg/ml stock in isopropanol were added to the HFBC-CM immediately prior to affinity chromatography. The material was run through the 266-affinity column at a flow rate of approximately 2 ml/min at 4° C. The column was then washed with 500 mls of PBS. Elution of material specifically bound to the resin was achieved with 0.2 M glycine pH 2.0. A total of 9 mls was used.

The eluted material was subjected to two steps of reversed phase liquid chromatography using a Vydac C4 [0.21×15 cm] reversed phase column and a solvent system containing 0.1% TFA in buffer "A" and 0.1% TFA/80% acetonitrile in buffer "B". The affinity-purified material was loaded onto the reversed phase column at 200 μl/min and then washed with 80% buffer (A) and 20% buffer "B" at 200 μl/min for 60 min and 50 μl/min for 42 min to equilibrate the column and stabilize the baseline. A gradient from 20% to 70% "B" was executed over 50 min at 50 μl/min, and the eluant was monitored at 0D$_{220}$. Fractions of 100 μl were collected and assayed by both Western blot and ELISA. Based on these results, fractions 11 and 12 were pooled and rechromatographed under nearly identical conditions except that a 150 min gradient from 10 to 40% "B" was employed followed by a 20 min gradient from 40 to 100% "B".

Figure 4:
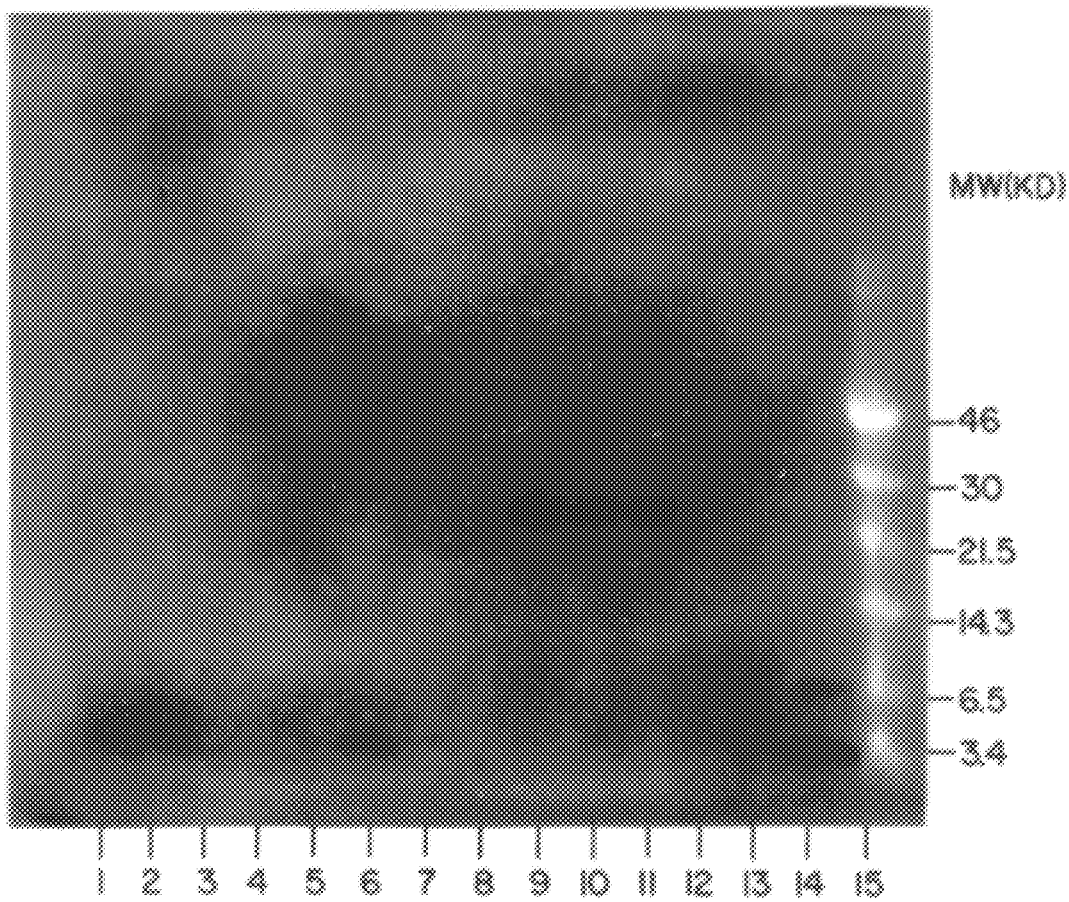
FIG. 4 is a Western blot of affinity-purified conditioned media from a cell line which overexpresses APP. The affinity-purified material from the conditioned media of human mixed-brain cell cultures which had been further purified by reversed-phase chromatography.

Fraction 77 from the second reversed phase chromatography step was found to be reactive against the 10D5 antibody by both Western blot (FIG. 4) and ELISA.

An aliquot of the material in fraction 77 was microsequenced and shown to have the N-terminal sequence of βAP, beginning with Asp. Microsequencing was performed on an Applied Biosystems Model 477 protein sequencer using a microscale reaction cartridge and Applied Biosystems's MICFST program cycles.

A second aliquot was subjected to electrospray ionization mass spectrometry, performed at M-SCAN, Inc., revealing a mass peak at 4329.81 (±1.27 SD) which would correspond to the expected mass of βAP$_{1-40}$ (theoretical MW of 4330.4). N-terminal sequencing of several of the A$_{220}$ peaks was positive for βAP. The ELISA revealed the βAP sequence to be present in fractions 65, 70, 75 in addition to the major peak in fraction 77. Fractions 65 and 70 contained an additional sequence of a previously undescribed βAP fragment beginning at βAP residue 11 (Glu). In fraction 65, sufficient material was present to sequence through βAP residue 33.

Western Blot (FIG. 4) of RPLC fractions of 266-affinity purified material from HFBC-CM. 3 μl of the indicated fractions were diluted with 15 μl of SDS-PAGE sample buffer and neutralized with 1 μl of 1 M NaOH before boiling and processing as described above. The material loaded in the respective lanes was as follows:

| Lane | RPLC fraction |
|---|---|
| 1 | 65 |
| 2 | 70 |
| 3 | 71 |
| 4 | 74 |
| 5 | 75 |
| 6 | 77 |
| 7 | 78 |
| 8 | 79 |
| 9 | 83 |

| Lane | RPLC fraction |
|---|---|
| 10 | 84 |
| 11 | 85 |

Lane 12 was buffer only; lane 13 contained 20 ng of βAP 1–38; lane 14 contains 100 ng of βAP 1–38; lane 15 contains low molecular weight Rainbows standards (Amersham). Note the approximate 4 kD band in lane 6 which co-migrates with the βAP standard in lane 14.

Parallel experiments to those described for HFBC-CM were performed using 4 liters of human CSF to structurally characterize the βAP immunoreactivity from this source. Sequencing data confirmed the presence of N-terminal sequences beginning with βAP residue 1 (Asp) and βAP residue 11 (Glu).

Figure 7:
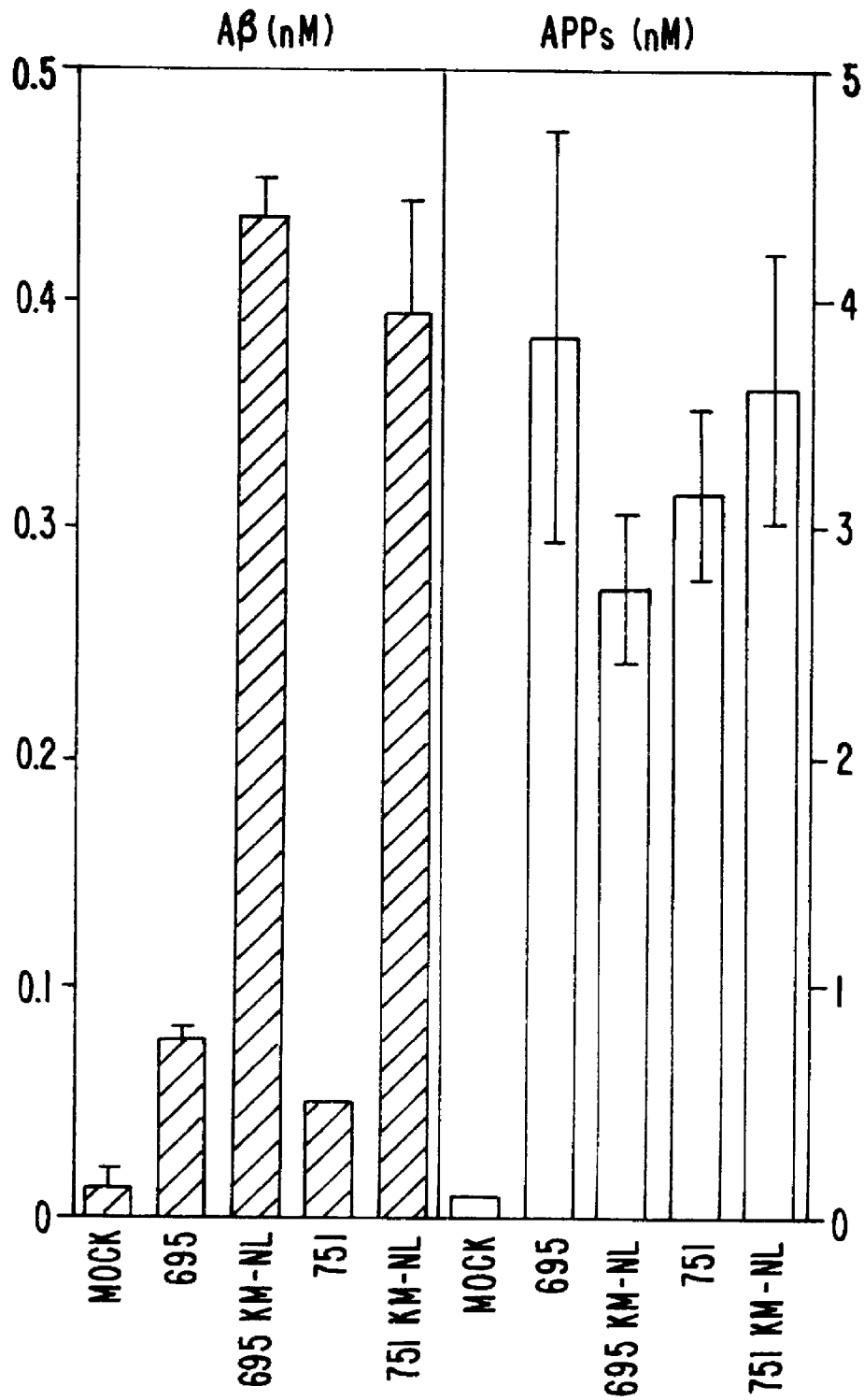
FIG. 7 shows the quantitation of βAP (left panel) and the secreted β-amyloid precursor protein (APPs) (right panel) in conditioned media in transiently transfected 293 cells using two distinct sandwich ELISAs. Each column represents the mean of four transfection experiments with normal or variant APP constructs with the exception of the mock column, which is based on three transfection experiments.

The increase in βAP levels in the media of the Swedish transfectants was quantitated using the βAP-specific ELISA with monoclonal antibodies 266 and 6C6. The sandwich ELISA for APP$_S$ used polyclonal antibodies B5 and B3. For each ELISA, increasing amounts of purified synthetic βAP$_{1-40}$ or purified APP$_S$ from conditioned media of K293 cells transfected with cDNA for the APP 695 isoform were used to construct a standard curve. Quantitation of βAP (left panel) and APP$_S$ (right panel) in conditioned media in the transiently transfected K293 cells is shown in FIG. 7. Each column represents the mean of four transfections with the exception of the mock column, which is based on three cultures. Error bars indicate the standard deviation. For columns without error bars, the standard deviation was less than 0.01 units.

As shown in FIG. 7, cells expressing the Swedish variant APP 695 construct produced 6–7 fold more βAP in their media than identically transfected cells expressing normal APP (695 isoform). Moreover, a similar 7–8 fold increase was observed in cultures expressing the Swedish mutation in the APP 751 isoform (FIG. 7). Similar increases in βAP levels were documented using a second method of quantitation: phosphor imager analysis of the 4 kD βAP band in gels of 1280 immunoprecipitates. This method further demonstrated that the 3 kD fragment was decreased several fold in the media of the Swedish transfectants. CHO and K293 cells stably transfected with cDNA the Swedish mutation in the APP 751 isoform also showed marked increases in the levels of βAP in their cultured media.

Figure 8:
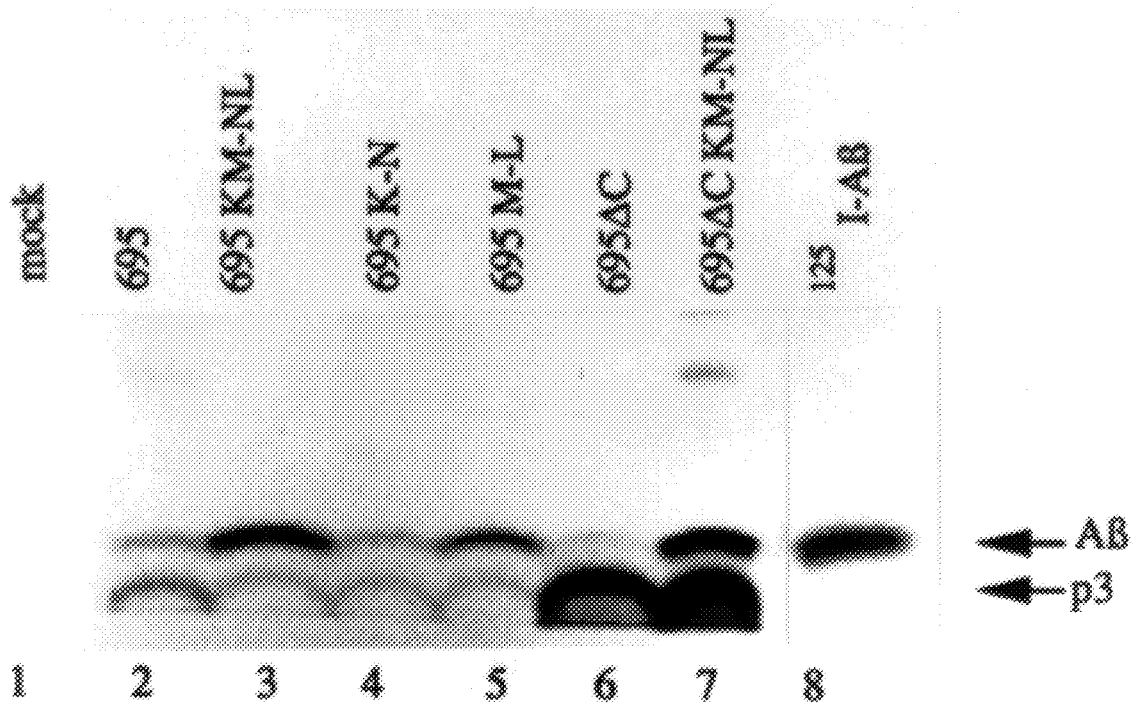
FIG. 8 is an autoradiogram demonstrating the levels of soluble βAP in the culture fluid of human kidney 293 cells transfected with normal or variant $APP_{695}$ constructs.

To study the mechanism responsible for the increased βAP production, the effects of each single mutation (Lys→Asn$^{595}$ and Met-Leu$^{596}$) in the APP 695 isoform were separately examined. FIG. 8 shows conditioned media of radiolabeled K293 cells transiently transfected with no DNA (lane 1); normal APP (lane 2), Swedish mutant APP 695 KM-NL (lane 3), variant APP 695 K-N (lane 4), variant APP 695 M-L (lane 5), APPAC (APP cytoplasmic domain deletion, lane 6) and APPAC KM-NL (Swedish mutations and cytoplasmic domain deletions, lane 7) and immunoprecipitated with 1280. The βAP and 3 kD bands are indicated by arrows. $^{125}$I-labeled synthetic βAP (1–40) was run as a size marker on the same gel (lane 8). Cells expressing the Met→Leu substitution had increased levels of βAP in their medium, whereas cells expressing the Lys→Asn substitution had levels similar to normal transfectants (FIG. 8, lanes 2–5). This finding suggests that the 596 mutation results in more proteolytic cleavage of APP at the Leu-Asp peptide bond than at the normal Met-Asp bond. It is possible that the Lys→Asn switch at 595 may further enhance the cleavage when coupled with the Met→Leu substitution at 596.

Cells containing the Swedish mutation together with the deletion of the cytoplasmic domain of APP deletion, thus removing the Asn-Pro-X-Tyr lysosomal targeting consensus sequence, still produced substantially more βAP in their media than normal transfectants but showed increased levels of the 3 kD peptide (FIG. 8, lanes 6 and 7). This result indicates that the effect of the Swedish mutations does not require an intact cytoplasmic domain and that generation of APP is unlikely to require processing of APP in late endosomes/lysosomes.

These findings provide experimental evidence that point mutations in the APP gene found in FAD kindreds can result directly in increased generation of βAP. Analysis of the Swedish mutations demonstrates the utility of measuring βAP production in vitro from APP bearing a particular mutation (e.g., mutations at residue 717 immediately following the βAP region and those within the βAP region) as not only a route to elucidating the mechanism of accelerated β-amyloidosis in familial forms of AD, but also to the utility of APP variants in the methods of the present invention.

Although the foregoing invention has been described in detail for purposes of clarity of understanding, it will be obvious that certain modifications may be practiced within the scope of the appended claims.

What is claimed is:

1. A method for reducing the production of soluble β-amyloid protein (βAP) in a mammalian host which expresses one or more APP isotypes and/or naturally occurring variants, said method comprising administering to the host an amount of a small molecule effective to reduce the amount of a soluble βAP present in a body fluid of the host.

2. A method as in claim 1, wherein the compound is administered orally, intramuscularly, intravenously, subcutaneously, or intraperitoneally.

3. A method as in claim 1, wherein the body fluid is selected from the group consisting of blood, CSF, urine, and peritoneal fluid.

4. A method as in claim 1, wherein the small molecule reduces the production of βP in cultured mammalian cells which produce soluble βAP.

5. A method as in claim 4, wherein the small molecule reduces the production of βAP in an assay comprising:

culturing mammalian cells in a culture medium under conditions which result in generation of soluble βAP which can be detected in the culture medium;

exposing the cultured cells to the small molecule; and measuring the reduction of soluble βAP present in the culture medium compared to soluble βAP present in the culture medium of non-exposed cultured mammalian cells.

6. A method as in claim 4, wherein the small molecule reduces the production of βAP in an assay comprising:

culturing a first population of mammalian cells in a culture medium under conditions which result in generation of a soluble βAP which can be detected in the culture medium;

culturing a second population of the same mammalian cells in second culture medium under identical conditions to the first population, except that the small molecule is present in the second culture medium;

specifically determining the amounts of soluble βAP present in the culture media of the first population and the second population of cells; and measuring the reduction of soluble βAP in the second culture medium as compared to the first culture medium.

7. A method for reducing soluble β-amyloid peptide (βAP) in a patient suffering from a β-amyloid peptide-related disease, said method comprising administering to the patient an amount of a small molecule effective to reduce the amount of βAP present in a body fluid of the patient.

8. A method as in claim 7, wherein the disease is Alzheimer's Disease.

9. A method as in claim 8, wherein the small molecule is administered orally, intramuscularly, subcutaneously, or intraperitoneally.

10. A method as in claim 8, wherein the body fluid is selected from the group consisting of blood, CSF, urine, and peritoneal fluid.

11. A method as in claim 8, wherein the small molecule reduces the production of βAP in cultured mammalian cells which produce βAP.

12. A method as in claim 11, wherein the small molecule reduces the production of βAP in an assay comprising:

culturing mammalian cells in a culture medium under conditions which result in generation of a soluble βAP which can be detected in the culture medium compared to soluble βAP present in the culture medium of non-exposed cultured mammalian cells;

exposing the cultured cells to the small molecule; and measuring the reduction of soluble βAP present in the culture medium.

13. A method as in claim 11, wherein the small molecule reduces the production of βAP in an assay comprising:

culturing a first population of mammalian cells in a culture medium under conditions which result in generation of a soluble βAP which can be detected in the culture medium;

culturing a second population of the same mammalian cells in second culture medium under identical conditions to the first population, except that the small molecule is present in the second culture medium;

specifically determining the amounts of soluble βAP present in the culture media of the first population and the second population of cells; and measuring the reduction of soluble βAP in the second culture medium as compared to the first culture medium.

14. A method for reducing the production of soluble β-amyloid protein (βAP) in a mammalian host which expresses one or more APP isotypes and/or naturally occurring variants, said method comprising:

(i) screening for small molecules that reduce the production of soluble βAP; and (ii) administering to the host an amount of the small molecule effective to reduce the amount of a soluble βAP present in a body fluid of the host.

* * * * *